(12) United States Patent
Minetti et al.

(10) Patent No.: US 7,078,521 B2
(45) Date of Patent: Jul. 18, 2006

(54) PROCESS FOR THE PREPARATION OF 9-AMINO SUBSTITUTED 9,10-DIHYDROPYRROLO[2,1-B][1,3] BENZOTIAZEPINES

(75) Inventors: Patrizia Minetti, Pomezia (IT); Domenico Mastrojanno, Pomezia (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 342 days.

(21) Appl. No.: 10/343,629

(22) PCT Filed: Jul. 20, 2001

(86) PCT No.: PCT/IT01/00391

§ 371 (c)(1),
(2), (4) Date: Feb. 3, 2003

(87) PCT Pub. No.: WO02/10174

PCT Pub. Date: Feb. 7, 2002

(65) Prior Publication Data

US 2003/0181437 A1    Sep. 25, 2003

(30) Foreign Application Priority Data

Aug. 1, 2000   (IT)   .................. RM2000A0434

(51) Int. Cl.
*C07D 513/04* (2006.01)
(52) U.S. Cl. .................... 540/547
(58) Field of Classification Search ............. 540/547
See application file for complete search history.

(56) References Cited

U.S. PATENT DOCUMENTS 6,391,870 B1 *  5/2002  Campiani et al. ...... 514/211.12

FOREIGN PATENT DOCUMENTS

WO     WO 00/06579     2/2000

OTHER PUBLICATIONS

Campiani et al., New Antipsychotic Agents with Serotonin Dopamine Antagonist Properties Based on a Pyrrolo[2,1-b][1,3]benzothiazepine Structure, Journal of Medicinal Chemistry, vol. 41, No. 20, pp. 3763-3772, Sep. 24, 1998.*

* cited by examiner

*Primary Examiner*—Brenda Coleman
(74) *Attorney, Agent, or Firm*—Nixon & Vanderhye P.C.

(57) ABSTRACT

A process is described for the preparation of compounds with the following formula where the groups are as defined below; in particular, $R_1$ is a substituted amine; said process includes essentially the reaction of pyrrolobenzothiazepin-9-one with amine $R_1H$ to give the corresponding enamine, which is subsequently transformed into the final compound

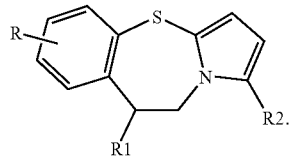

14 Claims, No Drawings

PROCESS FOR THE PREPARATION OF 9-AMINO SUBSTITUTED 9,10-DIHYDROPYRROLO[2,1-B][1,3] BENZOTIAZEPINES

This application is a national phase entry under 35 USC §371 of PCT/IT01/00391 filed Jul. 20, 2001.

The invention described herein relates to a process for the preparation of 9,10-dihydro-pyrrolo[2,1-b][1,3]benzothiazepines, and particularly 9-amino-substituted 9,10-dihydro-pyrrolo[2,1-b][1,3]benzothiazepines.

BACKGROUND TO THE INVENTION 9,10-Dihydro-pyrrolo[2,1-b][1,3]benzothiazepines are described in international patent application WO 00/06579, which is incorporated herein in its entirety for reference purposes, as compounds endowed with antipsychotic activity, with particular reference to the treatment of psychoses, such as schizophrenia, paranoid states, manic-depressive states, emotional disorders, antisocial behaviour, personality regression, and hallucinations.

For the compounds described in the patent application cited above, processes are provided for their preparation which involve the cyclisation reaction of a derivative containing a phenyl group and a pyrrol group, leading to the formation of a [1,3]-thiazepine ring. Preferably, the cyclisation should lead to a pyrrolo-benzothiazepinone derivative, which is then transformed into the desired 9-amino-substituted pyrrolo[2,1-b][1,3]benzothiazepine by acting on the ketone group.

The transformation of the ketone group to an amine group, optionally substituted, entails a certain number of steps. As illustrated in diagram 2B/2 of the patent application cited above, the ketone group is first reduced to a hydroxy group, which in turn is substituted with a suitable leaving group, for example a bromine atom, and finally the amine group desired is inserted. The transformation of the ketone group to a final amine group generates a chiral centre, and the resulting racemic mixture which derives from it is finally separated into the individual enantiomorphs with traditional methods. The substitution of the hydroxy group with the leaving group (bromine in the example given) entails a lowering of the yield, which the next step is unable to recover on a scale preparation plan.

SUMMARY OF THE INVENTION

It has now been found that it is possible to obtain 9-amino-substituted pyrrolo[2,1-b][1,3]benzothiazepines, starting from pyrrolobenzothiazepinone in a single step, allowing a much more interesting final yield of the product desired from the industrial point of view and with fewer impurities.

One object of the invention described herein is a process for the preparation of formula (I) compounds and their salts where:

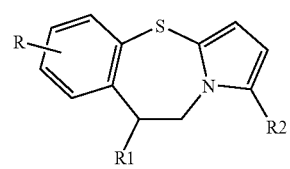

(I)

$R$=H, Cl, Br, F, I, $C_1$–$C_4$ alkoxy, $C_1$–$C_4$ alkylthio, $C_1$–$C_4$ alkyl, $C_5$–$C_6$ cycloalkyl;
$R_1$=dialkylamine, 4-alkyl-1-piperazinyl, 4-hydroxyalkyl-1-piperazinyl, 1-imidazolyl, 4-alkyl-1-piperidinyl
$R_2$=hydrogen, $C_1$–$C_4$ alkoxy, $C_1$–$C_4$ alkylthio;

essentially comprising the transformation of pyrrolobenzothiazepinone, substituted with groups R and $R_2$, into the formula (I) compound via the corresponding enamine, and optional salification with an acid.

DETAILED DESCRIPTION OF THE INVENTION

According to the invention described herein, the formula (Ia) compound

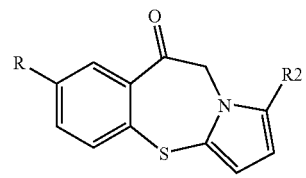

(Ia)

where R and $R_2$ are as defined above for the formula (I) compound is reacted with the desired amine $R_1H$ as defined for the $R_1$ group, to give the intermediate enamine (Ib)

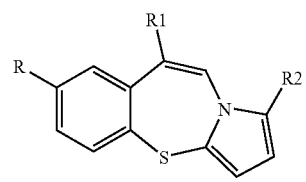

(Ib)

where $R_1$ is as defined above for the formula (I) compound, which is subsequently transformed into the final compound (I).

The transformation from compound (Ia) to (Ib) is accomplished with known techniques, but it has been seen that the reaction is conveniently achieved by treating compound (Ia) with the amine $R_1H$ in the presence of Lewis acids, for example triflates, such as trimethylsilyltrifluoromethane sulphonate, or protic acids, such as sulphonic acids, e.g. p-toluenesulphonic acid.

The reaction is carried out in a solvent which is inert to the reagents and the reaction products, or, in a preferred embodiment, the amine $R_1H$ can be used in relation to compound (Ia) in an excess such as to constitute the reaction medium. The reaction parameters are not critical and can be determined by a technician with average experience in the field on the basis of his or her own general knowledge of the subject. For example, the molar ratios of compound (Ia) to amine R₁H may range from 1:1 to an excess of amine in the sense referred to above. The reaction temperature will be selected also in relation to the type of reagents used, their molar ratios, and the optional presence of a solvent, in which case it may even be as high as the boiling temperature of the solvent, providing this does not lead to decomposition of the reagents themselves. The reaction times are selected on the basis of the parameters outlined above and will be such as to complete the reaction. Attempts to optimise the reaction do not constitute an additional experimental burden and are part of the normal techniques used in chemical synthesis.

The transformation of the enamine into the formula (I) compound is achieved by means of the reduction of the double enamine bond and falls within the sphere of the normal expertise of the average technician. Suitable reducing agents can be retrieved in the relevant literature manuals and do not require any particular specialist knowledge. For example, one suitable reducing agent is sodium borohydride. For this second step, too, the considerations outlined above regarding the reaction parameters and solvents hold good.

The isolation and purification of the formula (I) compound are accomplished with normal known procedures; in particular, the separation of the enantiomorphs can be done, amongst other things, as described in the above-mentioned patent application.

The process according to the invention described herein can be used to prepare benzothiazepines in general and, on proceeding with the reduction of the enamine, dihydrobenzothiazepines.

In a first preferred embodiment of the invention, the formula (Ia) compound is reacted with amine R₁H, using the latter as a reaction medium, when its physicochemical characteristics so permit. The triflate preferred is trimethylsilyltrifluoromethane sulphonate. The reaction temperature is approximately 120° C. and the reaction time approximately 3 hours.

In a second preferred embodiment of the invention, the formula (Ia) compound is reacted with amine R₁, using the latter as the reaction medium, when its physicochemical characteristics so permit. The preferred sulphonic acid is p-toluenesulphonic acid. The reaction temperature is approximately 180° C. and the reaction time approximately 1–2 hours.

The isolation and purification of the formula (I) compound are achieved with normal known procedures; in particular, the separation of the enantiomorphs can be accomplished, amongst other things, as described in the above-mentioned patent application, or, according to one embodiment of the invention described herein, by fractionated crystallisation.

The following examples further illustrate the invention.

Examples are provided for the preparation of (±)-7-chloro-9-(4-methylpiperazin-1-yl)-9,10-dihydropyrrolo[2,1-b][1,3]benzothiazepine (ST1455), one of the preferred compounds described in patent application WO 00/06579.

It is perfectly obvious that the examples provided here apply to all formula (I) compounds, with suitable modifications which can be implemented by the average technician in the field.

EXAMPLE 1 a) 7-chloro-9-(4-methyl-1-piperazinyl)pyrrolo [2,1b] [1,3] benzothiazepine (10b)

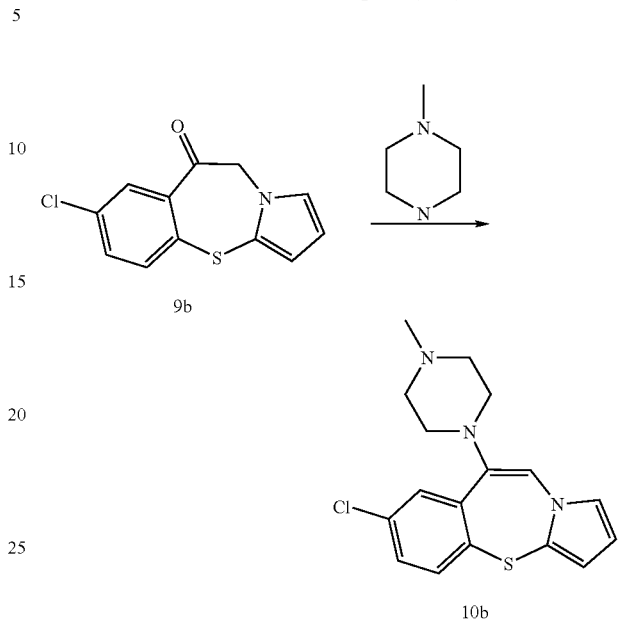

Procedure A)

To a mixture of ketone [9b] (4.5 g; 18 mmol) and N-methylpiperazine (15 mL) was added drop-wise trimethylsilyl-trifluoromethane sulphonate (5.7 mL; 31.5 mmol) in 5 minutes.

The reaction temperature was brought up to 120° C. The reaction, monitored via TLC, was completed in 3 hours. The reaction mixture was left to cool at ambient temperature and the resulting solid mass was dissolved in methylene chloride (50 mL) and washed with water (2×30 mL). The organic phase was anhydrified on sodium sulphate and filtered. Evaporation of the solvent at reduced pressure enabled a crude reaction product to be recovered, which, when chromatographed on silica gel (n-hexane/ethyl acetate 50:50) finally yielded 4.7 g of the title compound.

Yield: 78%

TLC (AcOEt) Rf=0.25; MP: 127÷128° C. ¹H-NMR (300 MHz, CDCl₃) δ 7.6 (d, 1H, J=2.1 Hz); 7.4 (d, 1H, J=8.5 Hz); 7.2 (dd, 1H, J₁=8.4 Hz, J₂=2.0 Hz); 6.7 (m, 1H); 6.6 (m, 1H); 6.2 (m, 1H); 6.1 (m, 1H); 2.9 (m, 4H); 2.6 (m, 4H); 2.3 (s, 3H). ¹³C-NMR (300 MHz CDCl₃) δ 143.8; 140.5; 137.9; 134.8; 133.2; 129.8; 129.6; 127.9; 123.2; 112.7; 111.6; 111.2; 55.2; 50.1; 46.2. Elemental analysis: (C₁₇H₁₈ClN₃S): compliant Procedure B)

A mixture of ketone [9b] (0.15 g; 0.6 mmol), N-methylpiperazine (0.18 g; 1.8 mmol) and p-toluenesulphonic acid (0.296 g; 1.56 mmol) was heated to 180° C.

The reaction, which rapidly took on a dark colouring, was completed in 1.5 hours; the mixture was left to cool at ambient temperature and the resulting-solid mass was dissolved in methylene chloride (10 mL) and washed with water (2×10 mL). The is organic phase was anhydrified on sodium sulphate and filtered. Evaporation of the solvent at reduced pressure yielded a crude reaction product which was chromatographed on silica gel (n-hexane/ethyl acetate 50:50) giving the title compound.

Preparation of the Compound b) (±)-7-chloro-9-(4-methylpiperazin-1-yl)-9,10-dihydropyrrol[2, 1-b][1,3]benzothiazepine (ST 1455)

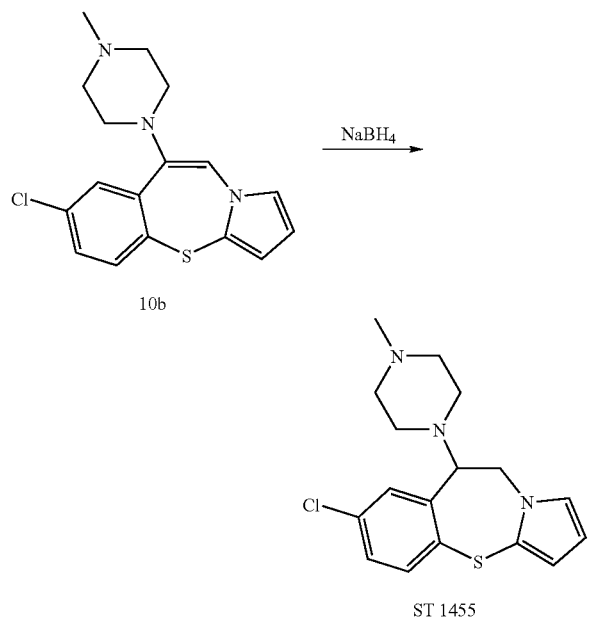

The compound [10b] (2.97 g; 8.97 mmol) was dissolved in acetic acid (25 mL); the solution was brought down to a temperature of 0° C. and NaBH$_4$ (400 mg) was added cautiously. The reaction was completed in 2 hours The mixture was evaporated at reduced pressure. Methylene chloride was added, and three washings with water and bicarbonate were done. The organic phase was anhydrified on sodium sulphate, filtered and evaporated at reduced pressure. 2.75 g of product were obtained with 95% purity, as calculated at HPLC.

Yield: 87%

The tables given here below show the values of the individual process steps according to the invention described herein (Table 1) as compared to the process described in patent, application WO 00/06579; see in particular pp. 29–30 and example 2 of the patent application cited (Table 2).

TABLE 1

| Transformation (substrate → product) | Transformation yield (%) |
|---|---|
| [9b] → [10b] | 78 |
| [10b] → [ST1455] | 87 |
| Total transformation yield: 9.6 | |

TABLE 2

| Transformation (substrate → product) | Transformation yield (%) |
|---|---|
| [9b] → [24b] | 88 |
| [24b] → [25b] | 51 |

TABLE 2-continued

| Transformation (substrate → product) | Transformation yield (%) |
|---|---|
| [25b] → [ST1455] | 68 |
| Total transformation yield: 4.3 | |

EXAMPLE 2

Separation of Racemic Mixture by Fractionated Crystallisation of ST1455

The racemic mixture obtained was separated into the two optically active isomers by means of fractionated crystallisation of the diastereoisomeric salts obtained by salification with tartaric acid, according to the procedure outlined here below.

2.5 g of ST1455 (7.5 mmol) were dissolved hot in ethanol and added with 1.12 g of D(−) tartaric acid (7.5 mmol). The solution was held overnight at ambient temperature. The tartrate crystals thus obtained were filtered and recrystallised by a 3:1 ethanol/methanol mixture. The solution was held overnight-at ambient temperature. After filtration, 1.1 g of tartrate of the (+) enantiomorph were obtained, which at HPLC presented an optical purity of 97.3.

Column: Chiralpack-AD (5 m), 4.6×250 mm; T=23° C.; mobile phase: n-hexane-ethanol, TEA (95/5/0.1 v/v); flow: 1 ml/min; Rt=5.6 min Yield: 62%

The tartrate was then converted to a free base by treatment with NaHCO$_3$ and extraction by AcOEt.

Similarly, ST1455 was treated with L(+) tartaric acid to yield the corresponding tartrate of the (−) enantiomorph.

The method of separating the racemic mixture by fractionated crystallisation is particularly advantageous compared to that obtained by separation on a semipreparative chiral column, whenever the amounts of product required are considerably greater than those normally deriving from a laboratory synthesis process.

The invention claimed is:

1. A process for the preparation of formula (I) or its salt

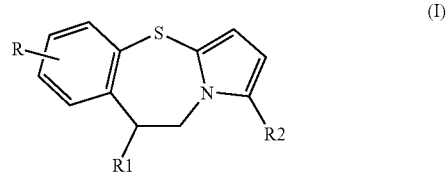

where:

R is selected from the group consisting of H, Cl, Br, F, I, C$_1$–C$_4$ alkoxy, C$_1$–C$_4$ alkylthio, C$_1$–C$_4$ alkyl, C$_5$–C$_6$ cycloalkyl;

R1 is selected from the group consisting of dialkylamine, 4-alkyl-1-piperazinyl group, 4-hydroxyalkyl-1-piperidinyl group, 1-imidazolyl group, 4-alkyl-1-piperidinyl group;

R2 is selected from the group consisting of hydrogen, a C$_1$–C$_4$ alkoxy group, and a C$_1$–C$_4$ alkylthio group, by transforming a pyrrolobenzothiazepinone, substituted with the groups R and R2, into the formula (I) compound to the corresponding enamine, and optional salifying the compound with an acid.

2. A process for the preparation of formula (I) or its salt

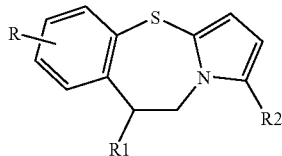
(I)

where:

R is selected from the group consisting of H, Cl, Br, F, I, $C_1$–$C_4$ alkoxy, $C_1$–$C_4$ alkylthio, $C_1$–$C_4$ alkyl, $C_5$–$C_6$ cycloalkyl;

R1 is selected from the group consisting of a dialkylamine, a 4-alkyl-1-piperazinyl group, a 4-hydroxyalkyl-1-piperazinyl group, a 1-imidazolyl group, and 4-alkyl-1-piperidinyl group;

R2 is selected from the group consisting of hydrogen, a $C_1$–$C_4$ alkoxy group, and a $C_1$–$C_4$ alkylthio group, by reacting a pyrrolobenzothiazepinone of formula (Ia)

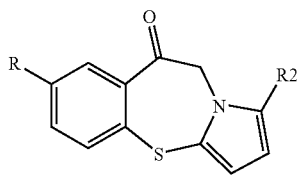
(Ia)

with an amine R1H, wherein R1 is as defined above to give a compound of formula (Ib)

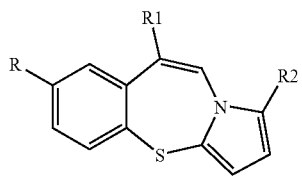
(Ib)

which is subsequently transformed into the final compound (I), and optionally salified with an acid.

3. Process according to claim 2, in which compound (Ia) and amine R1H are reacted in the presence of a Lewis acid.

4. Process according to claim 3, in which said acid is a triflate.

5. Process according to claim 4, in which said triflate is trimethylsilyltrifluoromethane sulphonate.

6. Process according to claim 2, in which compound (Ia) and amine R1H are reacted in the presence of a protic acid.

7. Process according to claim 6, in which said acid is a sulphonic acid.

8. Process according to claim 7, in which said sulphonic acid is p-toluenesulphonic acid.

9. Process according to any one of claims 2, in which amine R1H can be used in relation to compound (Ia) in an excess such as to constitute the reaction medium.

10. Process according to any one of claims 2, in which enamine (Ib) is transformed into compound (I) by means of a reducing agent.

11. Process according to claim 10, in which said reducing agent is sodium borohydride.

12. Process according to claim 5, in which the reaction temperature is approximately 120° C. and the reaction time approximately 3 hours.

13. Process according to claim 6, in which the reaction temperature is approximately 180° C. and the reaction time approximately 1–2 hours.

14. Process according to claim 2, in which the formula (I) compound is separated into enantiomorphs.

* * * * *

UNITED STATES PATENT AND TRADEMARK OFFICE
CERTIFICATE OF CORRECTION

PATENT NO. : 7,078,521 B2  Page 1 of 1
APPLICATION NO. : 10/343629
DATED : July 18, 2006
INVENTOR(S) : Minetti et al.

It is certified that error appears in the above-identified patent and that said Letters Patent is hereby corrected as shown below:

On Title Page

Item (75) Patrizia Minetti, Pomezia (IT) should read

--Domenico Mastroianni, Pomezia (IT)--

Col. 6, Line 45 should read

--1. A process for the preparation of a compound of formula (I) or its salt

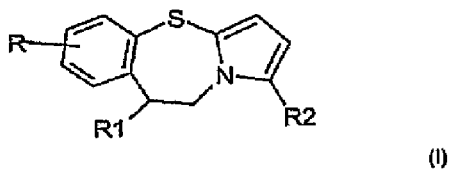

(I)

where:

R is selected form the group consisting of H, Cl, Br, F, I, $C_1$-$C_4$ alkoxy, $C_1$-$C_4$ alkylthio, $C_1$-$C_4$ alkyl, and $C_5$-$C_6$ cycloalkyl;

R1 is selected form the froup consisting of a dialkylamine, 4-alkyl-1-piperazinyl group, 4-hydroxyalkyl-l-piperazinyl group, 1-imidazolyl group, and 4-alkyl-1-piperidinyl gorup;

R2 is selectd from the group consisting of hydrogen, a $C_1$-$C_4$ alkoxy group, and a $C_1$-$C_4$ alkylthio group, by transforming a pyrrolobenzothiazepinone, substituted with the groups R and R2, in the formula (I) compound to the corresponding enamine, and optionally salifying the compound with an acid. --

Signed and Sealed this

Twenty-sixth Day of December, 2006

JON W. DUDAS
*Director of the United States Patent and Trademark Office*